United States Patent [19]
Iversen

[11] Patent Number: 5,902,236
[45] Date of Patent: May 11, 1999

[54] TISSUE ELECTRODE FOR RECORDING AND STIMULATION

[75] Inventor: Alfred Abner Iversen, Wayzata, Minn.

[73] Assignee: PMT Corporation, Chanhassen, Minn.

[21] Appl. No.: 08/922,902

[22] Filed: Sep. 3, 1997

[51] Int. Cl.$^6$ ................................ A61B 5/042; A61N 1/05
[52] U.S. Cl. .......................... 600/377; 600/378; 600/393; 607/116; 607/117
[58] Field of Search ..................................... 600/378, 377, 600/373, 393; 607/117, 116

[56] References Cited

U.S. PATENT DOCUMENTS

| | | |
|---|---|---|
| 4,374,527 | 2/1983 | Iversen . |
| 4,461,304 | 7/1984 | Kuperstein .............................. 600/378 |
| 4,735,208 | 4/1988 | Wyler et al. . |
| 4,869,255 | 9/1989 | Putz . |

OTHER PUBLICATIONS

Subdural Strip Electrodes for Localizing Epleptogenic Foci, Joural of Neurosurgery, Jun. 1984, vol. 60, pp. 1195–1200.

Primary Examiner—Lee Cohen
Attorney, Agent, or Firm—Anthony G. Eggink

[57] ABSTRACT

An improved tissue electrode for monitoring tissue electrical activity and for tissue electrical stimulation and adapted to conform closely to the tissue, thereby optimizing tissue electrical contact. The electrode consists of an elongated electrode body with a polygonal cross-section with a tissue-engaging surface having a pair of tissue-engaging members confronting each other at an obtuse angle and a non-tissue-engaging surface meeting each of the tissue-engaging members at an acute angle. In one embodiment, the non-tissue-engaging surface is substantially flat, and the electrode thus is a half-rhombus in cross-section. In a second embodiment, the non-tissue-engaging surface is also a half-rhombus, so that the electrode is a rhombus in cross-section. An improved electrical connector for connecting lead wires from the electrode to external monitoring equipment is also disclosed. A device for inserting the electrode into body tissue is also disclosed, the device having a stylet pre-curved to conform to the tissue and a sheath surrounding the stylet for receiving the electrode.

17 Claims, 4 Drawing Sheets

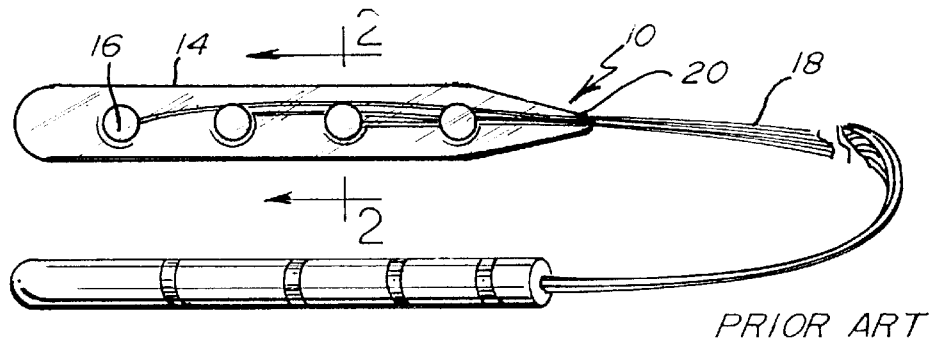
Fig. 1. PRIOR ART
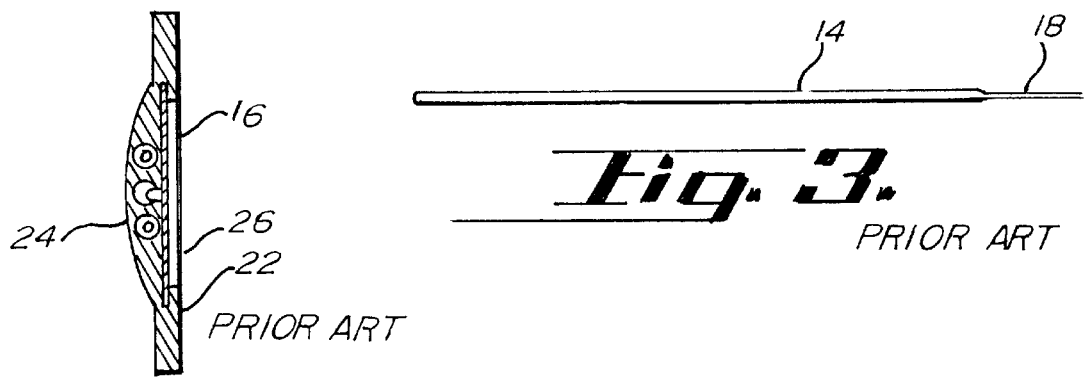
Fig. 2. PRIOR ART
Fig. 3. PRIOR ART
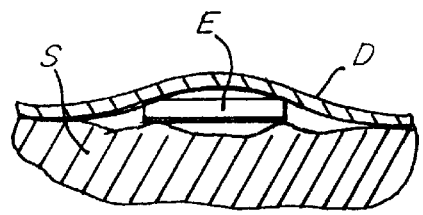
Fig. 5. PRIOR ART
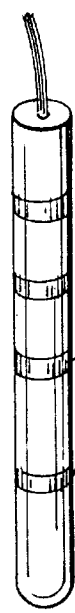
Fig. 4. PRIOR ART
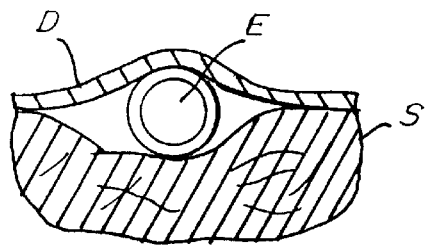
Fig. 6. PRIOR ART

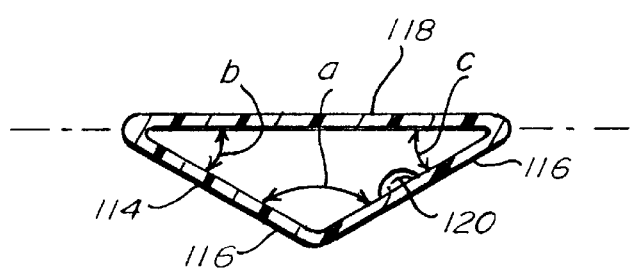
_Fig. 11._
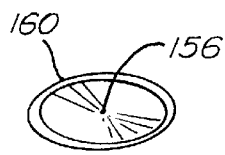
_Fig.13a._
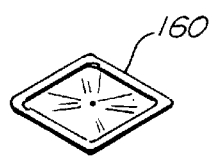
_Fig.13b._
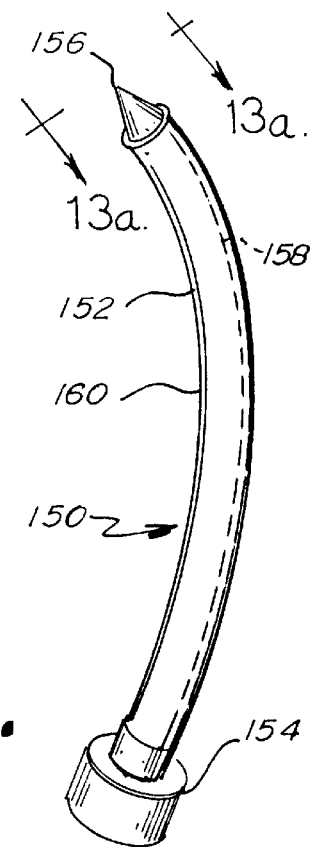
_Fig.12._
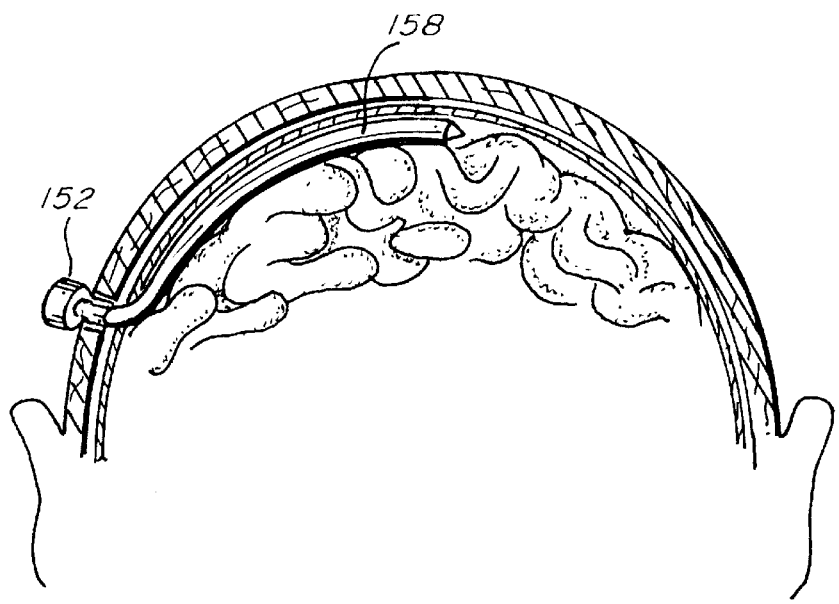
_Fig.14._

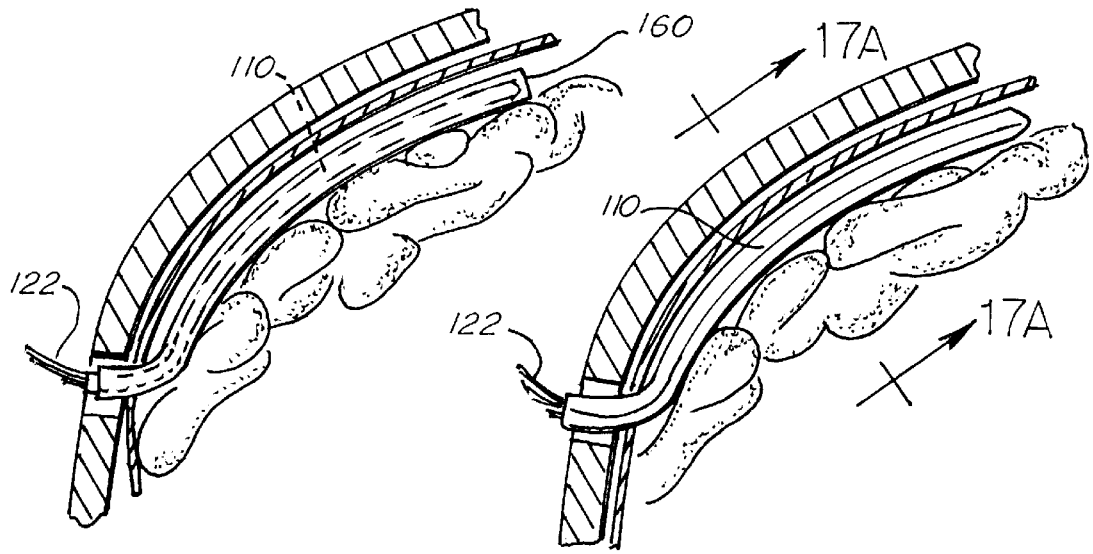
_Fig.15._     _Fig.16._
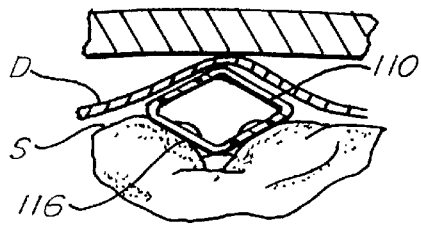     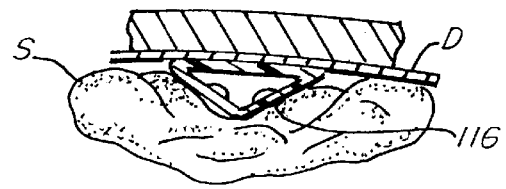
_Fig.17A_     _Fig.17B._
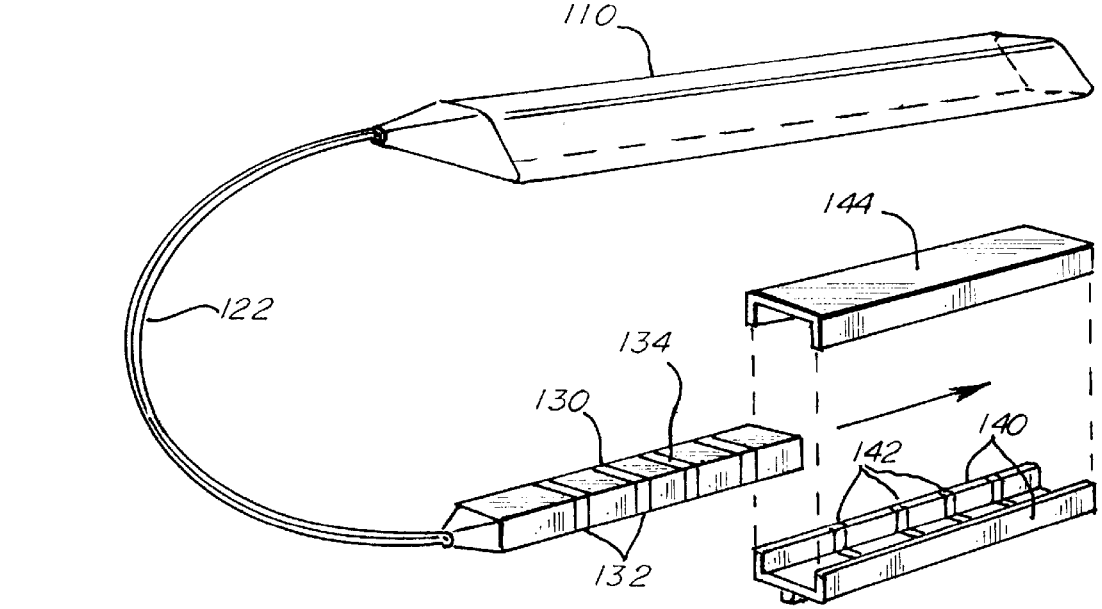
_Fig.18._

TISSUE ELECTRODE FOR RECORDING AND STIMULATION

BACKGROUND OF THE INVENTION

This invention is related generally to electrodes for monitoring cortical electrical activity in order to define epileptogenic foci. However, the invention is not limited to monitoring brain electrical activity but also has improved features for monitoring and electrical stimulation of other tissue. For example, the invention may be used to monitor electrical activity in or to stimulate the spinal cord.

Surgical removal of epileptogenic brain is indicated for treatment of many medically refractory focal seizure disorders. One of the important factors in providing good results from such surgery is the degree of accuracy in identifying epileptogenic foci. Various methods have been used in attempting to determine epileptogenic foci, and all, of course, involve sensing of cortical electrical activity using electrical contacts applied in various ways.

Standard scalp contacts have been used for many years, but accurate localization is usually very difficult with recordings obtained from such contacts. Therefore, many epilepsy centers in recent years have used intracranial recording techniques to better define regions of cortical epileptogenicity.

Intracranial recording techniques have used either of two different types of electrodes—intracortical depth electrodes or subdural strip electrodes. The far more commonly used technique of intracranial recording uses intracortical depth electrodes, but other techniques using subdural strip electrodes, first utilized many years ago, have been shown to be relatively safe and valuable alternatives.

The relative safety of subdural strip electrodes lies in the fact that, unlike depth electrodes, they are not invasive of brain tissue. Depth electrodes are narrow, typically cylindrical dielectric structures with contact bands spaced along their lengths. Such electrodes are inserted into the brain in order to establish good electrical contact with different portions of the brain. Subdural strip electrodes, on the other hand, are generally flat strips supporting contacts spaced along their lengths. Such strip electrodes are inserted between the dura and the brain, along the surface of and in contact with the brain, but not within the brain.

A typical subdural strip electrode of the prior art is shown in FIGS. 1–4 and is disclosed in U.S. Pat. No. 4,735,208. The '208 patent discloses a subdural strip electrode 10 having an elongated flexible silicone dielectric strip 14, a plurality of spaced aligned flat electrical stainless steel contact disks 16 held within dielectric strip 14, and lead wires 18 exiting strip 14 from a proximal end 20 thereof.

Dielectric strip 14 of strip electrode 10 has front and back dielectric layers 22 and 24, respectively. Each front layer 22 has a front layer opening 26 for each contact disk 16. Openings 26 are circular and somewhat smaller in diameter than contact disks 16. Front and back layers 22 and 24 are sealed together by adhesive and/or heat such that they form, in essence, an integral dielectric strip.

As can be seen in FIGS. 2 and 3, the subdural strip electrodes of the prior art are predominately rectangular in cross-section. Other subdural strip electrodes of the prior art have a circular or round cross section.

As can be seen in FIGS. 5 and 6, prior art subdural strip electrodes that have a rectangular (FIG. 5) or round (FIG. 6) cross-section do not optimize the amount of surface area of the electrode E in contact with the cortical surface S. As the electrode E is inserted between the dura D and the cortical surface S, downward pressure is exerted by the dura on the electrode, which in turn exerts pressure on the cortical surface. Such pressure causes the cortical surface S to slightly deflect downward, as shown in the Figures. Prior art rectangular or round electrodes cannot follow this deflection, resulting, in the case of a rectangular electrode (FIG. 5), in the electrode contacting the surface S primarily at the edges; and in the case of the round electrode (FIG. 6), in the electrode contacting the surface S along an arc.

One of the problems with such prior art strip electrodes is that the lack of adequate contact with the brain surface can result in inaccurate recordings of epileptogenic foci.

Another problem with such prior art strip electrodes is that there is very little room between the dielectric strips to pass the wires. This may require very fine wires with high electrical resistance, which may in turn cause inaccurate recordings.

Another problem of such prior art strip electrodes is lack of adequate stiffness for insertion. It would seem that proper insertion of the strip electrode requires at least some degree of stiffness (less than complete flexibility) in the strip, because of how such strips are inserted through the burr hole and under the dura. That is, rather than being pulled into place between the dura and the brain by grasping the distal end of the strip, such strips must be pushed into place from their proximal ends from which the lead wires extend. Nothing supports the strip along its length much beyond the edge of the burr hole during the complete insertion step. It is understood that if there is insufficient stiffness along the strip length and across the strip width, the strip could not be inserted properly. In some cases, it could stray from the intended position; in other cases, it could turn or double up.

Proper insertion and positioning and having an accurate understanding of the exact positions of the strip are essential to proper interpretation of the recordings taken from the strip contacts. For that reason, it has been thought necessary to have a certain amount of strip thickness and width in order to provide the necessary body or stiffness for proper insertion.

Another consideration in the design of subdural strip electrodes is their ability to adequately support the contacts and lead wires secured by the dielectric strip. If insufficient dielectric supporting material encompasses the contacts and lead wires, the lead wires when pulled could distort the strip and create undesirable openings in the strip. The lead wires would also be more prone to break away and the contacts more prone to be mislocated within the strip.

All of these factors argue for greater width and thickness dimensions in the strip electrode—that is, greater cross-sectional area. Yet, there has been a trend in the subdural strip electrode art to decrease cross-sectional area.

A problem resulting from low mass and low cross-sectional area in subdural strip electrodes is that they are not easily seen under X-ray.

The lead wires are generally routed out through a stab wound in the skin remote from the electrode and generally terminate in a distal end with ring-type terminals (FIG. 4). These ring-type terminals are then connected to monitoring equipment by means of a connector. Such a prior connector is disclosed in U.S. Pat. No. 4,869,255. FIG. 7 illustrates such a connector of the prior art.

The connector 20 holds several pairs of male conductor members 34 in an array. The lead wire terminal rings 32 of the electrode and male conductor members 34 are held in engagement by mechanical interference. As can be seen in FIG. 7, this arrangement results in the lead wire terminal rings 32 making contact with the male conductor members 34 only along two short arcs. This minimal surface area may result in inaccurate electrical recordings of cortical activity.

There is a need for an improved tissue electrode and connector which addresses the above problems of prior art electrodes.

SUMMARY OF THE INVENTION

An improved tissue electrode for monitoring tissue electrical activity and for tissue electrical stimulation and adapted to conform closely to the tissue, thereby optimizing tissue electrical contact. The electrode consists of an elongated electrode body with a polygonal cross-section with a tissue-engaging surface having a pair of tissue-engaging members confronting each other at an obtuse angle and a non-tissueengaging surface meeting each of the tissue-engaging members at an acute angle. In one embodiment, the non-tissue-engaging surface is substantially flat, and the electrode thus is a half-rhombus in cross-section. In a second embodiment, the nontissue-engaging surface is also a half-rhombus, so that the electrode is a rhombus in cross-section. An improved electrical connector for connecting lead wires from the electrode to external monitoring equipment is also disclosed. A device for inserting the electrode into body tissue is also disclosed, the device having a stylet pre-curved to conform to the tissue and a sheath surrounding the stylet for receiving the electrode.

A principal object and advantage of the present invention is that the electrode has a tissue-engaging surface adapted to closely conform to the tissue as the electrode is inserted in the tissue, thereby maximizing electrical contact with the tissue.

A feature of the present invention is that the tissue-engaging surface is in the form of two tissue-engaging members meeting each other at an obtuse angle, and a non-tissue-engaging surface meeting the tissue-engaging members at an acute angle. By varying the acute angles, and thereby indirectly varying the obtuse angle, the amount of tissue-engaging surface in contact with the tissue can be optimized.

A feature of the invention is that the non-tissue-engaging surface is flat in one embodiment, so that the electrode is a half-rhombus in cross-section. Advantageously, the flat surface provides a tactile guide to the surgeon to ensure that the tissue-engaging surface is placed in contact with the tissue.

A feature of the invention is that in one embodiment the electrode is a rhombus in cross-section.

A second principal object and advantage of the present invention is that the electrode provides substantial internal space for lead wires, so that the lead wires may be thicker and thus less easily broken and have less electrical resistance.

Another object and advantage of the present invention is that the electrode has substantial mass and stiffness, so that the electrode may be accurately inserted and will not turn or double up during insertion.

Another object and advantage of the present invention is that the electrode has substantial mass and thickness so that it shows up readily on X-ray, thereby allowing accurate placement.

Another object and advantage of the present invention is that the lead wire terminals are square in cross-section and an improved electrical connector is provided which also has a square cross-section for mating with the lead wire terminals. The square cross-section improves electrical contact.

Another object and advantage of the present invention is that it provides an improved tool for inserting the electrode into body tissue. The insertion tool consists of a stylet with a shaft that is pre-curved to conform to the tissue and a sheath which is left in the tissue after the stylet is removed. The electrode is threaded through the sheath into the tissue. In a preferred embodiment, the stylet is pre-curved with the average radius of the adult human skull, so that the stylet follows the skull contour during insertion under the dura, thus preventing the stylet from straying and inadvertently piercing brain tissue while at the same time allowing easy insertion.

BRIEF DESCRIPTION OF THE DRAWINGS

FIG. 1 is an top view of a prior art subdural strip electrode.

FIG. 2 is a cross-section along the lines 2 of FIG. 1.

FIG. 3 is a side elevational view of the prior art electrode of FIG. 1.

FIG. 4 is a perspective view of a terminal mount and lead wire terminals of the prior art.

FIG. 5 is a sectional view of a rectangular prior art electrode inserted between the dura and the brain surface.

FIG. 6 is a sectional view of a round prior art electrode inserted between the dura and the brain surface.

FIG. 11 is a cross-section along the lines 11 of FIG. 10.

FIG. 12 is a perspective view of the improved insertion tool of the present invention.

FIGS. 13A and 13B are cross-sections along the lines 13 of FIG. 12, showing two different embodiments.

FIG. 14 is a cross-section of the human skull and brain showing the insertion tool of the present invention being inserted between the dura and the brain surface.

FIG. 15 is a cross-section of the human skull and brain showing the stylet being removed and the sheath left in place between the dura and the brain surface.

FIG. 16 is a cross-section of the human skull showing the electrode being threaded through the sheath to contact the brain surface.

FIG. 17A is a sectional view along the lines 17A of FIG. 16, showing the full-rhombus electrode inserted between the dura and the brain surface.

FIG. 17B is a sectional view showing the half-rhombus electrode inserted between the dura and the spinal cord.

FIG. 18 is a perspective view showing the square lead wire terminal rings of the present invention contacting the square conductor array of the present invention.

DETAILED DESCRIPTION OF THE PREFERRED EMBODIMENTS

Figure 7:
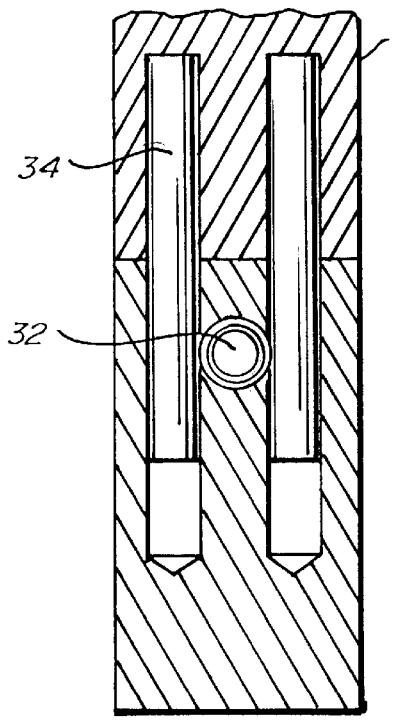
FIG. 7 is a sectional view of an electrical connection device of the prior art.

The improved tissue electrode of the present invention is shown in the figures as reference numeral 110.

Figure 9:
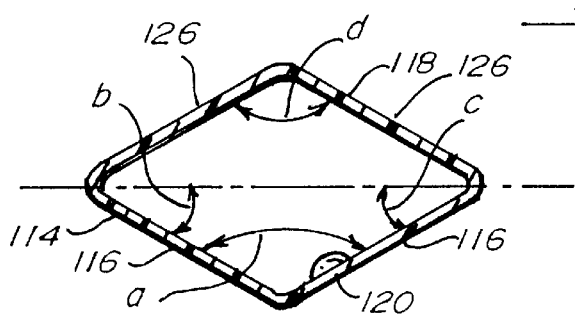
FIG. 9 is a cross-section along the lines 9 of FIG.8.

The tissue electrode 110 consists of an elongated electrode body 112 having a tissue-engaging surface 114 with a pair of tissue-engaging members 116 confronting each other at an obtuse angle (a, FIGS. 9 and 11) and a non-tissueengaging surface 118 meeting each of the tissue-engaging members 116 at an acute angle (b, c FIGS. 9 and 11).

A plurality of electrical contact areas 120 are found along on the tissue-engaging surface 114 for making electrical contact with the tissue.

Lead wires 122 engage the electrical contact areas 120 and exit the electrode body 112 at the proximal end 124.

The acute angles (b, c) between the non-tissue-engaging surface 118 and the tissue-engaging members 116 are optimized to promote maximal contact between the tissue-engaging surface 114 and the tissue.

As the electrode 110 is inserted between the dura D and the cortical surface S, for example, downward pressure is exerted by the dura on the electrode, which in turn exerts pressure on the cortical surface. Such pressure causes the cortical surface to deflect slightly downward. If the angles (b, c) are correct, the tissueengaging members 116 will follow this deflection, as best shown in FIG. 17A, resulting in maximal contact between the tissue-engaging surface 114 and the tissue. While this example addresses the brain, the same principles are applicable to any application in which the electrode is inserted between tissue layers. For example, FIG. 17B shows how the electrode 110 can provide maximum contact with the spinal cord surface when inserted between the dura D and the spinal cord surface S.

Our studies have found that angles of over 30 degrees and under 5 degrees are not valuable. Over 30 degrees provides a too-obtrusive angle and too much bulk to the electrode. Under 5 degrees does not provide enough mass to the electrode body.

Figure 10:
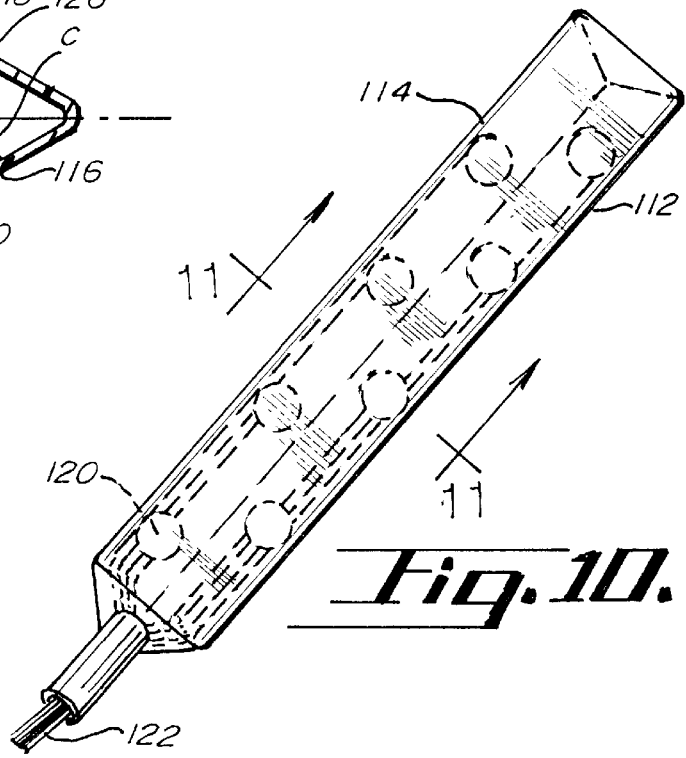
FIG. 10 is a perspective view of the improved tissue electrode of the present invention in the shape of a half-rhombus.

In the preferred embodiment (FIGS. 10, 11), the electrode 110 has the shape of a half-rhombus in cross-section. In this embodiment, the non-tissue-engaging surface 118 is substantially flat. The preferred range of the angles (b, c) is 5 degrees to 30 degrees. For some applications, the most preferred range is 5 degrees to 15 degrees. This embodiment has the advantage of providing a tactile guide to the surgeon to ensure that the tissue-engaging surface 114 is placed in contact with the tissue to be monitored. For example, the surgeon may place a finger on the flat, non-tissue-engaging surface 118 while inserting the electrode 110 between the dura and brain, so that the non-tissue-engaging surface 118 confronts the dura and the tissue-engaging surface 114 confronts the brain. This effectively prevents the electrode from being inserted "upside down", as is possible with prior art subdural strip electrodes, which might avoid the necessity of re-opening the incision to correct the mistake.

Figure 8:
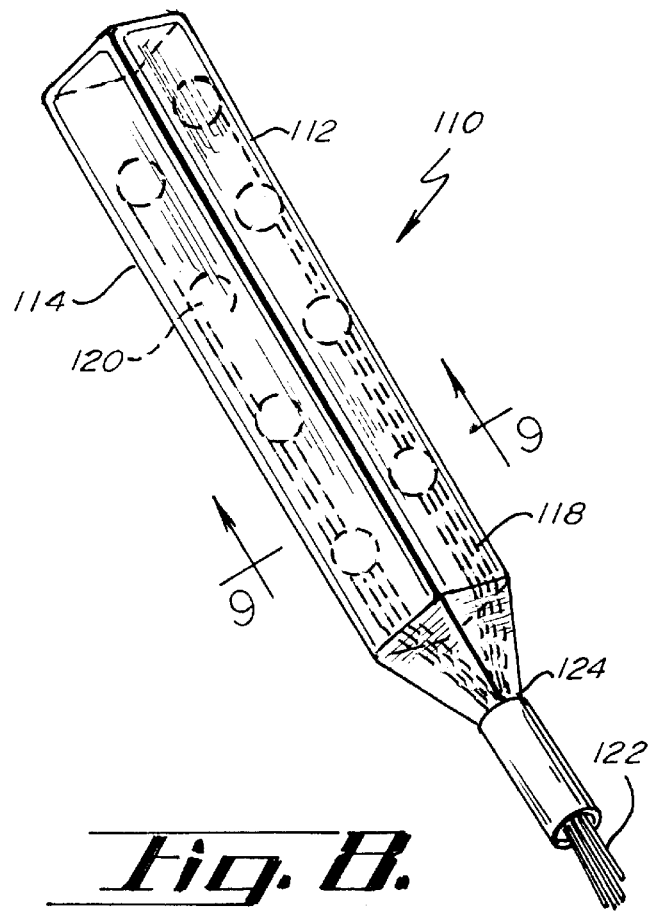
FIG. 8 is a perspective view of the improved tissue electrode of the present invention in the shape of a rhombus.

In another embodiment (FIGS. 8, 9) the electrode 110 has the shape of a rhombus (an equilateral parallelogram) in cross-section. In this embodiment, the non-tissue-engaging surface 118 further comprises a pair of non-tissue engaging members 126 confronting each other at an obtuse angle (d, FIG. 9). Preferably, the length of the non-tissue-engaging members 126 is substantially equal to the length of the tissue-engaging members 116. In this embodiment, the angles (b, c) are measured between the central axis of the electrode and the tissue-engaging members 116, as shown in FIG. 9.

The tissue electrode 110 of the present invention has the further advantage that the interior of the rhombus or half-rhombus provides much more room for the lead wires 122. This allow the use of thicker wires with corresponding lower electrical resistance, which may result in more accurate recordings.

The improved tissue electrode 110 also provides more stiffness for insertion than prior art electrodes. The polygonal cross-section of the electrode 110 makes the electrode substantially more stiff than prior art subdural strip electrodes. That is, the polygonal cross-section provides support to the electrode body 112 along its length during the complete insertion step. This prevents the electrode 110 from turning or doubling up during insertion.

The improved tissue electrode 110 also provides substantially more mass than prior art electrodes so that it shows up under X-ray much more readily, allowing more accurate placement.

The electrode body 112 is preferably composed of a material selected from the group consisting of silicone rubber, latex, and polyurethane.

The electrical contact areas 120 may be any material which conducts an electrical current. Preferably, the electrical contact areas are a conductive metal, such as platinum, platinum/iridium, silver, or stainless steel. Alternatively, the electrical contact areas may be a conductive polymer or latex.

The tissue electrode 110 may also preferably have a plurality of terminal contacts 132 engaging the lead wires 122, the terminal contacts each having flat sides for engaging a flat-sided electrical connector. Preferably, the terminal contacts 132 are square in cross-section and are inserted into an electrical connector 140 which is also square in cross-section (FIG. 18).

Preferably, the lead wires 122 extent to a terminal mount 130 and to an array of lead-wire terminals 132 on and forming a part of the terminal mount 130, the terminal mount 130 and lead-wire terminals 132 having a square cross-section. The lead-wire terminals 132 engage an array of individual conductors 142 on a conductor support 140 which holds the individual conductors 142 in a conductor array. Preferably, a connector block 144 receives the terminal mount 130 and lead-wire terminals 132, the connector block 144 engaging the conductor support 140.

The square cross-section of the lead-wire terminals 132 and electrical connector 140 promotes much better electrical contact than prior art connectors.

The invention also includes an improved device 150 for inserting the tissue electrode into body tissue for electrical monitoring and stimulation (FIGS. 12–17).

The improved insertion tool 150 comprises a stylet 152 having a first end 154 adapted for gripping and a second sharp end 156 for tunnelling through tissue and a shaft 158 interconnecting the first end 154 and second end 156. A hollow sheath 160 surrounds the stylet 152 and the stylet is removable from the sheath 160. The shaft 158 is pre-curved to conform to the tissue and the sheath 160 is left in the tissue after the stylet 152 is removed and the tissue electrode 110 is threaded through the sheath 160. Then the sheath 160 is removed, leaving the electrode 110 in place in the tissue to be monitored.

The sheath may be malleable and adapted to conform to the tissue.

For use in epileptogenic foci monitoring, the shaft 158 preferably has a radius substantially equivalent to the radius of curvature of the adult human skull. Most preferably, the shaft has a radius in the range of 1.5 inches to 2 inches. In this embodiment, the stylet 152 follows the skull contour during insertion under the dura, thus preventing the stylet 152 from straying and inadvertently piercing brain tissue, while at the same time allowing easy insertion.

The cross-section of the sheath may be any shape which allows insertion of the electrode 110. The cross-section may be elliptical (FIG. 13A) or rhombus-shaped (FIG. 13B).

FIG. 14 shows the stylet 152 being inserted through a burr hole in the skull and the pre-curved shape of the shaft 158 following the skull contour. In FIG. 15, the stylet 152 has been removed, leaving the sheath 160 in place, and the electrode 110 has been threaded through the sheath 158. In FIG. 16, the sheath 160 has been removed and the electrode 110 is left in contact with the brain surface.

The present invention may be embodied in other specific forms without departing from the spirit or essential attributes thereof, and it is therefore desired that the present embodiment be considered in all respects as illustrative and not restrictive, reference being made to the appended claims rather than to the foregoing description to indicate the scope of the invention.

What is claimed:

1. An improved tissue electrode for monitoring tissue electrical activity and for tissue electrical stimulation and adapted to conform closely to the tissue, thereby optimizing tissue electrical contact, the electrode comprising:
   (a) an elongated electrode body with a polygonal cross-section, the electrode body further comprising a tissue-engaging surface having a pair of tissue-engaging members confronting each other at an obtuse angle and a non-tissue-engaging surface meeting each of the tissue-engaging members at an acute angle;
   (b) a plurality of electrical contact areas along the tissue-engaging surface for making electrical contact with the tissue; and
   (c) lead wires engaging the electrical contact areas and exiting the electrode body from a proximal end portion
the acute angle between the non-tissue-engaging surface and the tissue-engaging members being optimized to promote maximal contact between the tissue-engaging surface and the tissue.

2. The electrode of claim 1, wherein the non-tissue engaging surface is substantially flat and the acute angle is in the range of 5 degrees to 30 degrees.

3. The electrode of claim 2, wherein the non-tissue engaging surface is substantially flat and the acute angle is in the range of 5 degrees to 15 degrees.

4. The electrode of claim 1, wherein the non-tissue-engaging surface further comprises a pair of non-tissue-engaging members confronting each other at an obtuse angle.

5. The electrode of claim 4, wherein the length of the non-tissue-engaging members is substantially equal to the length of the tissue-engaging members, so that the cross-section of the electrode is a rhombus.

6. The electrode of claim 1, wherein the electrode is a subdural electrode for insertion between the dura and the brain, the non-tissue-engaging surface confronting the dura and the tissue-engaging surface confronting the brain.

7. The electrode of claim 1, wherein the electrode is a subdural electrode for insertion between the dura and the spinal cord, the non-tissue-engaging surface confronting the dura and the tissue-engaging surface confronting the spinal cord.

8. The electrode of claim 1, wherein the electrode body is composed of a material selected from the group consisting of silicone rubber, latex, and polyurethane.

9. The electrode of claim 1, wherein the electrical contact areas are a conductive metal.

10. The electrode of claim 9, wherein the electrical contact areas are of a material selected from the group consisting of platinum, platinum/iridium, silver, and stainless steel.

11. The electrode of claim 1, wherein the electrical contact areas are a conductive polymer.

12. An improved tissue electrode for monitoring tissue electrical activity and for tissue electrical stimulation and adapted to conform closely to the tissue, thereby optimizing tissue electrical contact, the electrode comprising:
   (a) an elongated electrode body with a polygonal cross-section, the electrode body further comprising a tissue-engaging surface having a pair of tissue-engaging members confronting each other at an obtuse angle and a non-tissue-engaging surface meeting each of the tissueengaging members at an acute angle;
   (b) a plurality of electrical contact areas along the tissue-engaging surface for making electrical contact with the tissue;
   (c) lead wires engaging the electrical contact areas and exiting the electrode body from a proximal end portion; and
   (d) a plurality of terminal contacts engaging the lead wires, the terminal contacts each having flat sides adapted to engage a flat-sided electrode connector
the acute angle between the non-tissue-engaging surface and the tissue-engaging members being optimized to promote maximal contact between the tissue-engaging surface and the tissue.

13. The electrode of claim 12, wherein the non-tissue engaging surface is substantially flat and the acute angle is in the range of 5 degrees to 30 degrees.

14. The electrode of claim 13, wherein the non-tissue engaging surface is substantially flat and the acute angle is in the range of 5 degrees to 15 degrees.

15. The electrode of claim 12, wherein the non-tissue-engaging surface further comprises a pair of non-tissue-engaging members confronting each other at an obtuse angle.

16. The electrode of claim 15, wherein the length of the non-tissue-engaging members is substantially equal to the length of the tissue-engaging members, so that the cross-section of the electrode is a rhombus.

17. The electrode of claim 12, wherein the terminal contacts have a square cross-section and the connector has a square cross-section.

* * * * *